(12) United States Patent
Ayame et al.

(10) Patent No.: US 8,300,093 B2
(45) Date of Patent: Oct. 30, 2012

(54) ENDOSCOPE IMAGE PROCESSING METHOD AND APPARATUS, AND ENDOSCOPE SYSTEM USING THE SAME

(75) Inventors: Daisuke Ayame, Saitama (JP); Shuichi Ishii, Saitama (JP); Shinji Takeuchi, Saitama (JP); Hiroshi Fujita, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 648 days.

(21) Appl. No.: 12/352,387

(22) Filed: Jan. 12, 2009

(65) Prior Publication Data
US 2010/0177181 A1 Jul. 15, 2010

(51) Int. Cl.
*A61B 1/06* (2006.01)
(52) U.S. Cl. ......................................................... 348/71
(58) Field of Classification Search ...................... 348/71
See application file for complete search history.

(56) References Cited

U.S. PATENT DOCUMENTS

| | | | | |
|---|---|---|---|---|
| 5,972,716 A * | 10/1999 | Ragusa et al. | ................. | 436/172 |
| 6,028,622 A * | 2/2000 | Suzuki | ............................. | 348/65 |
| 6,293,911 B1 | 9/2001 | Imaizumi et al. | | |
| 6,537,211 B1 * | 3/2003 | Wang et al. | .................... | 600/178 |
| 7,330,749 B1 * | 2/2008 | Bhunachet | .................... | 600/476 |
| 2002/0035330 A1 * | 3/2002 | Cline et al. | ..................... | 600/476 |
| 2002/0128557 A1 * | 9/2002 | Hohla et al. | .................... | 600/476 |
| 2002/0161282 A1 * | 10/2002 | Fulghum | ......................... | 600/160 |
| 2003/0078477 A1 | 4/2003 | Kang et al. | | |
| 2003/0158470 A1 * | 8/2003 | Wolters et al. | ................. | 600/317 |
| 2003/0191368 A1 * | 10/2003 | Wang et al. | .................... | 600/160 |
| 2004/0186351 A1 * | 9/2004 | Imaizumi et al. | ............. | 600/160 |
| 2004/0257438 A1 * | 12/2004 | Doguchi et al. | ................. | 348/65 |
| 2005/0059894 A1 * | 3/2005 | Zeng et al. | ..................... | 600/476 |
| 2006/0052710 A1 * | 3/2006 | Miura et al. | ................... | 600/476 |
| 2006/0197831 A1 | 9/2006 | Takeuchi et al. | | |
| 2006/0241496 A1 * | 10/2006 | Fengler et al. | ................ | 600/476 |
| 2006/0241499 A1 * | 10/2006 | Irion et al. | ..................... | 600/476 |
| 2007/0088192 A1 | 4/2007 | Takeuchi et al. | | |
| 2009/0114803 A1 * | 5/2009 | Yamaguchi | .................... | 250/226 |
| 2009/0147998 A1 * | 6/2009 | Yamaguchi et al. | .......... | 382/106 |
| 2009/0147999 A1 * | 6/2009 | Maeda et al. | ................. | 382/106 |
| 2009/0289200 A1 * | 11/2009 | Ishii | ........................... | 250/459.1 |
| 2010/0067002 A1 * | 3/2010 | Ishii | .............................. | 356/317 |
| 2010/0130870 A1 * | 5/2010 | Kopriva | ........................ | 600/476 |

(Continued)

FOREIGN PATENT DOCUMENTS

EP 1 964 503 A1 9/2008

(Continued)

OTHER PUBLICATIONS

EP Communication, dated Jun. 22, 2009, issued in corresponding EP Application No. 09000306.2, 5 pages.

(Continued)

*Primary Examiner* — Imad Hussain
(74) *Attorney, Agent, or Firm* — Sughrue Mion, PLLC

(57) ABSTRACT

A method capable of obtaining a fluorescence image and a background image with a simple configuration. A color image is obtained, when excitation light is emitted on a subject, by imaging excitation light reflected from the subject and fluorescence emitted from the subject. Thereafter, an estimated spectral image that includes a background image representing the excitation light and a fluorescence image representing the fluorescence is generated by allocating a wavelength component of the excitation light and a wavelength component of the fluorescence included in the obtained color image to different primary color components.

9 Claims, 6 Drawing Sheets

U.S. PATENT DOCUMENTS

2010/0305436 A1* 12/2010 Chen et al. .................. 600/431
2011/0042580 A1* 2/2011 Wilson et al. .............. 250/458.1

FOREIGN PATENT DOCUMENTS

| | | |
|---|---|---|
| JP | 10-201707 A | 8/1998 |
| JP | 2000-270265 A | 9/2000 |
| JP | 2002-291682 A | 10/2002 |
| JP | 2003-093336 A | 4/2003 |
| JP | 2003-204924 A | 7/2003 |
| JP | 2004-024392 A | 1/2004 |
| JP | 2006-239205 A | 9/2006 |
| JP | 2007-029453 A | 2/2007 |
| JP | 2007-105291 A | 4/2007 |

OTHER PUBLICATIONS

Notification of Grounds for Rejection, dated Jun. 19, 2012, issued in corresponding JP Application No. 2007-305385, 6 pages in English and Japanese.

* cited by examiner

FIG.3

| PARAMETERS $P_i$ | $kr_i$ | $kg_i$ | $kb_i$ |
|---|---|---|---|
| $P_1$ | −0.0000144 | −0.0000193 | 0.0000192 |
| $P_2$ | −0.0000136 | −0.0000202 | 0.0000181 |
| $P_3$ | −0.0000108 | −0.0000174 | 0.0000152 |
| $P_4$ | −0.0000114 | −0.0000171 | 0.0000157 |
| $P_5$ | −0.0000124 | −0.0000167 | 0.0000173 |
| $P_6$ | −0.0000154 | −0.0000211 | 0.0000232 |
| $P_7$ | −0.0000227 | −0.0000328 | 0.0000365 |
| $P_8$ | −0.0000384 | −0.0000555 | 0.0000642 |
| $P_9$ | −0.0000708 | −0.0000963 | 0.0001214 |
| $P_{10}$ | −0.0001276 | −0.0001494 | 0.0002176 |
| $P_{11}$ | −0.0001757 | −0.0001620 | 0.0002957 |
| $P_{12}$ | −0.0000716 | −0.0000489 | 0.0001206 |
| $P_{13}$ | −0.0000097 | −0.0000042 | 0.0000150 |
| $P_{14}$ | −0.0000086 | −0.0000041 | 0.0000112 |
| $P_{15}$ | −0.0000113 | 0.0000019 | 0.0000141 |
| $P_{16}$ | −0.0000145 | 0.0000105 | 0.0000180 |
| $P_{17}$ | −0.0000150 | 0.00000039 | 0.0000187 |
| $P_{18}$ | −0.0000160 | 0.0000402 | 0.0000182 |
| ... | ... | ... | ... |
| $P_{61}$ | 0.00548 | −0.00229 | 0.00453 |

Columns $P_1$–$P_{14}$ span $\Delta\lambda_1$ (=400~465nm); columns $P_{15}$–$P_{18}$ span $\Delta\lambda_2$ (=470~700nm).

ENDOSCOPE IMAGE PROCESSING METHOD AND APPARATUS, AND ENDOSCOPE SYSTEM USING THE SAME

BACKGROUND OF THE INVENTION

1. Field of the Invention

The present invention relates to an endoscope image processing method and apparatus for observing fluorescence emitted from a subject when exposed to excitation light. The invention also relates to an endoscope system using the same.

2. Description of the Related Art

It is known that a living tissue emits self fluorescence when exposed to excitation light of a certain wavelength. Consequently, an endoscope apparatus that emits excitation light on a living tissue in a body cavity and observes self fluorescence emitted from the living tissue is proposed. Here, when observing the fluorescence, a fluorescence image that indicates the emission state of fluorescence and a background image that indicates the exposure state of excitation light are required in order to compare a region on which the excitation light is emitted and a region from which the fluorescence is emitted.

Here, it is known that excitation light reflected from the subject and the fluorescence are spectrally separated from each other by half prism, band-pass filter, or the like, and the excitation light and fluorescence are imaged by separate imaging devices. Further, a method in which a barrier filter that blocks excitation light and transmits fluorescence and a barrier filter that blocks the fluorescence and transmits the excitation light are switched at a constant period to obtain a fluorescence image of the fluorescence and a background image of the excitation light at different times is proposed as described, for example, in Japanese Unexamined Patent Publication No. 2000-270265.

Imaging of a fluorescence signal and a background signal by separate imaging devices poses a problem that it requires a plurality of imaging devices and other optical components, such as a half prism and the like, resulting in a complicated system configuration. Further, where a fluorescence image and a background image are obtained in a time-series manner as described in Japanese Unexamined Patent Publication No. 2000-270265, a difference in spatial position may occur between the background image and fluorescence image if the subject moves, thereby posing a problem that accurate diagnosis is prevented.

In view of the circumstances described above, it is an object of the present invention to provide an endoscope image processing method and apparatus, and an endoscope system capable of obtaining a fluorescence image and a background image with a simple system configuration.

SUMMARY OF THE INVENTION

An endoscope image processing method of the present invention is a method, including the steps of:

obtaining a color image, when excitation light is emitted on a subject, by imaging excitation light reflected from the subject and fluorescence emitted from the subject; and generating an estimated spectral image that includes a background image representing the excitation light and a fluorescence image representing the fluorescence by allocating a wavelength component of the excitation light and a wavelength component of the fluorescence included in the obtained color image to different primary color components.

An endoscope image processing apparatus of the present invention is an apparatus, including:

an image obtaining unit for obtaining a color image, when excitation light is emitted on a subject, by imaging excitation light reflected from the subject and fluorescence emitted from the subject; and a spectral image generation unit for generating an estimated spectral image that includes a background image representing the excitation light and a fluorescence image representing the fluorescence by allocating a wavelength component of the excitation light and a wavelength component of the fluorescence included in the obtained color image to different primary color components.

An endoscope system of the present invention is a system, including:

a light source unit for emitting excitation light on a subject;

a scope for guiding the excitation light emitted from the light source unit to the subject and having an imaging device for imaging, when the excitation light is emitted on the subject, excitation light reflected from the subject and fluorescence emitted from the subject; and an endoscope image processing apparatus for extracting a fluorescence image from a subject image obtained by the scope, wherein the endoscope image processing apparatus includes:

an image obtaining unit for obtaining a color image taken by the imaging device; and a spectral image generation unit for generating an estimated spectral image that includes a background image representing the excitation light and a fluorescence image representing the fluorescence by allocating a wavelength component of the excitation light and a wavelength component of the fluorescence included in the obtained color image to different primary color components.

Here, the fluorescence may be any fluorescence emitted when exposed to excitation light. For example, it may be self fluorescence emitted from a living tissue produced by the fluorescent component inherent to the living tissue which is weak light in a wavelength range from green to red when exposed to excitation light of a blue wavelength range. Alternatively, it may be fluorescence of wavelengths adjacent to 636 nm imaged by emitting excitation light with a wavelength of about 405 nm on 5-aminolevulinic acid (ALA). Otherwise, it may be, for example, fluorescence of wavelengths adjacent to 840 nm imaged by emitting excitation light of 780 nm wavelength on indocyanine green (ICG) injected inside of a body cavity.

Further, only the fluorescence image or background image may be displayed on a display device by displaying each of the primary color components of the estimated spectral image separately.

The endoscope image processing apparatus may further include a gamma correction unit for performing gamma correction on the color image obtained by the image obtaining unit. Here, the spectral image generation unit is a unit for generating the estimated spectral image using the color image gamma-corrected by the gamma correction unit.

The spectral image generation unit may be a unit for allocating the wavelength range of the fluorescence to any primary color component of the estimated spectral image of RGB components. For example, it may be a unit for generating the estimated spectral image by allocating the wavelength component of the excitation light to R and B signals to produce the background image and the wavelength component of the fluorescence to G signal to produce the fluorescence image.

The spectral image generation unit may be a unit having a function to generate a sub-fluorescence image of a wavelength range from about 500 to 550 nm (green) from the color image or the estimated spectral image, other than the function to generate the estimated spectral image. Here, the endoscope image processing apparatus may further include a lesion image generation unit for calculating, with respect to each pixel, the ratio of the pixel value of the sub-fluorescence image to the pixel value of the fluorescence image as a lesion index, and generating a lesion index image colored based on the calculated lesion index values.

Further, the scope may further include a cut filter disposed on the light receiving surface side of the imaging device to reduce the amount of light in the wavelength range of the excitation light received by the imaging device.

According to the endoscope image processing method and apparatus, and endoscope system using the same, when excitation light is emitted on a subject, a color image is obtained by imaging excitation light reflected from the subject and fluorescence emitted from the subject, and an estimated spectral image is generated in which a wavelength component of the excitation light and a wavelength component of the fluorescence included in the obtained color image are allocated to different primary color components. This allows generation of the background image and fluorescence image from the color image based on wavelength information of the excitation light and fluorescence without separate imaging devices as required in the past, whereby emission state of the fluorescence may be checked with a simple configuration.

Further, where gamma correction unit for performing gamma correction on the color image obtained by the image obtaining unit is provided, and spectral image generation unit is a unit for generating the estimated spectral image using the color image gamma-corrected by the gamma correction unit, signal values representing excitation light in the estimated spectral image may be reduced, and signal values representing fluorescence in the estimated spectral image may be increased. This allows generation of an estimated spectral image enhanced in the fluorescence portion.

Still further, where the excitation light has a blue wavelength range and fluorescence is self fluorescence, the spectral image generation unit is a unit having a function to generate sub-fluorescence image of a green wavelength range from the color image or estimated spectral image, and lesion image generation unit for calculating, with respect to each pixel, the ratio of the pixel value of sub-fluorescence image to the pixel value of fluorescence image as a lesion index and generating a lesion index image colored based on the calculated lesion index values is further included, accurate fluorescence diagnosis may be made by taking note of the fact that a normal area has a higher proportion of intensity in a green wavelength range in the wavelength range of self fluorescence in comparison with a lesion area, and visualizing the ratio of the green wavelength range from 500 to 550 nm in the fluorescence as a lesion index image.

Further, where the scope further includes a cut filter disposed on the light receiving surface side of the imaging device to reduce the amount of light in the wavelength range of the excitation light received by the imaging device, then even when the emission amount of the excitation light is increased in order to increase the emission amount of fluorescence, the imaging device may be prevented from saturating, whereby the excitation light and fluorescence may be imaged accurately.

BRIEF DESCRIPTION OF THE DRAWINGS

FIG. 3 is an example data chart of the matrix data base in FIG. 1.

DESCRIPTION OF THE PREFERRED EMBODIMENTS

Figure 1:
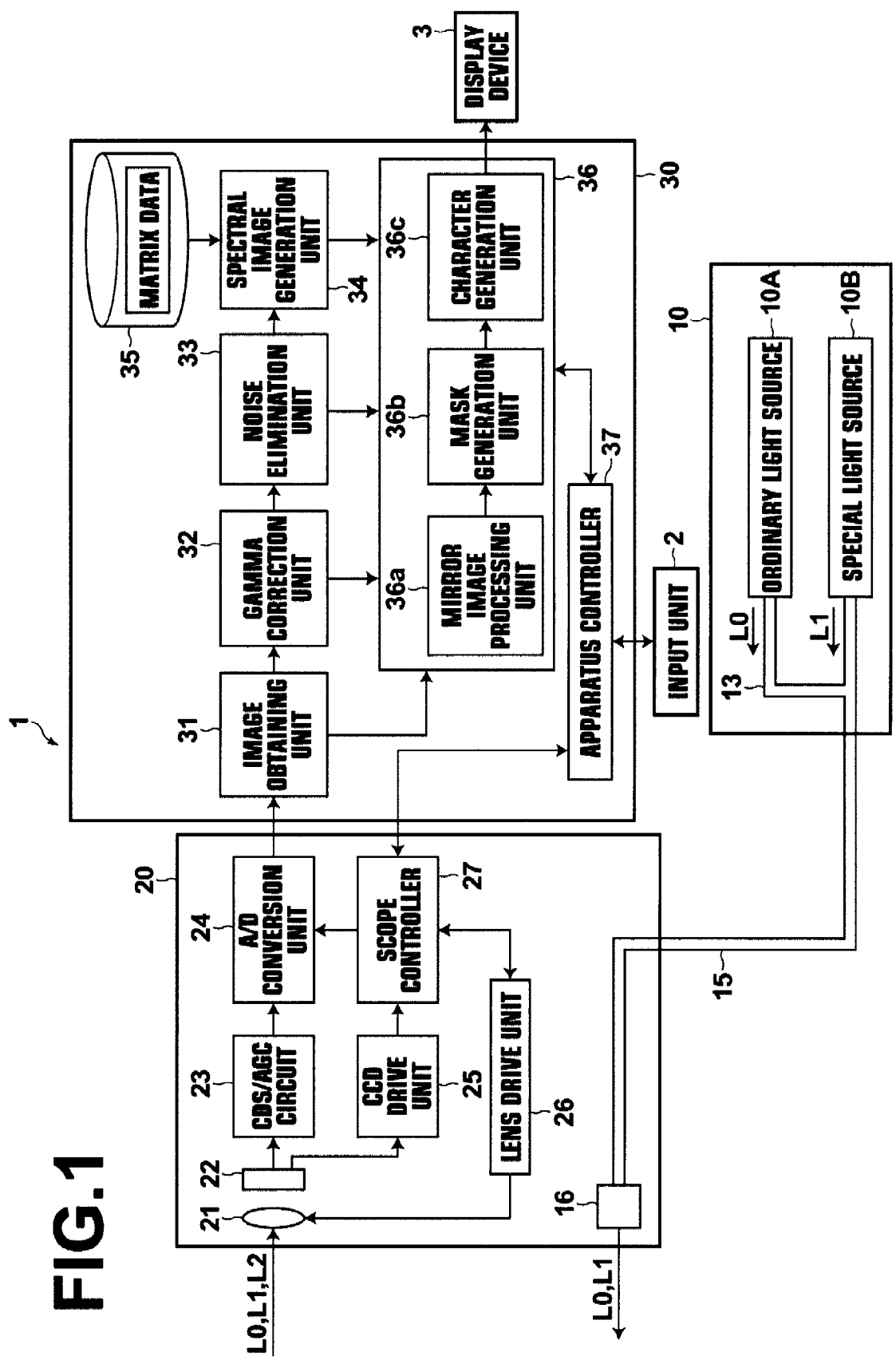
FIG. 1 is a block diagram of the endoscope image processing apparatus according to an exemplary embodiment of the present invention.

Hereinafter, embodiments of the present invention will be described with reference to the accompanying drawings. FIG. 1 illustrates a basic configuration of endoscope system 1 according to an embodiment of the present invention. Endoscope system 1 includes light source unit 10, scope 20, and endoscope image processing apparatus 30. Light source unit 10 is a unit for emitting light required for performing observation with an endoscope and includes ordinary light source 10A of a xenon lamp or the like that emits ordinary light L0 for ordinary observation, and a special light source 10B of a visible laser device or the like that emits excitation light L1 for fluorescence observation. Light source unit 10 is optically connected to light guide 15 of scope 20, and ordinary light L0 emitted from ordinary light source 10A is inputted to light guide 15 at the time of ordinary observation and excitation light L1 emitted from light source 10B is inputted to light guide 15 at the time of fluorescence observation. Ordinary light L0 and excitation light L1 are emitted on a subject from observation window 16 through light guide 15.

Scope 20 includes imaging optics 21, imaging device 22, CDS/AGC circuit 23, A/D conversion unit 24, CCD drive unit 25, lens drive unit 26, and the like, each of which is controlled by scope controller 27. Imaging device 22 includes, for example, CCD, CMOS, or the like, and obtains color image P by photoelectrically converting a subject image formed by imaging optics 21. As for imaging device 22, for example, a complementary color imaging device having color filters of Mg (magenta), Ye (yellow), Cy (cyan), and G (green) or a primary color imaging device having RGB color filters on the image forming surface is used. The operation of imaging device 22 is controlled by CCD drive unit 25. When an image (picture) signal is captured by imaging device 22, the signal is sampled and amplified by CDS/AGC (correlated double sampling/automatic gain control) circuit 23, then color image P outputted from CDS/AGC circuit 23 is A/D converted by A/D conversion unit 24, and the A/D converted color image is outputted to endoscope image processing apparatus 30.

It is noted that a band cut filter that blocks light in the wavelength range of excitation light L1 at the time of fluorescence observation may be provided on the light receiving surface side of imaging device 22 in scope 20 in order to prevent imaging device 22 from saturating.

An exemplary embodiment of the endoscope image processing apparatus of the present invention will now be described with reference to FIG. 1. Endoscope image processing apparatus 30 is an apparatus for performing image processing on a color image outputted from scope 20, and includes image obtaining unit 31, gamma correction unit 32, noise elimination unit 33, spectral image generation unit 34, display control unit 36, and the like.

Image obtaining unit 31 includes, for example, a DSP (digital signal processor) or the like, and obtains excitation light L1 reflected from a subject when excitation light L1 is emitted thereon and fluorescence L2 self fluoresced in the subject by receiving excitation light L1 captured by imaging device 22 in scope 20 as color image P. When color image P of Mg (magenta), Ye (yellow), Cy (cyan), and G (green) is obtained, image obtaining unit 31 has a function to convert it to a RGB color image.

Figure 2:
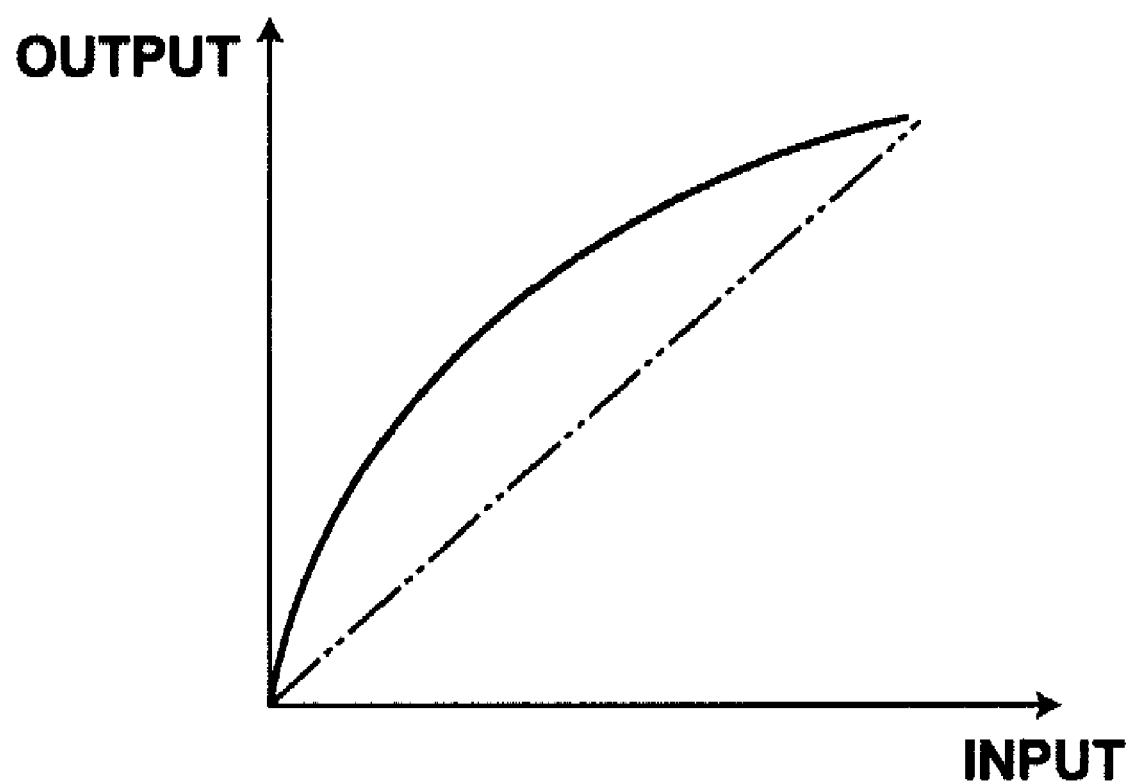
FIG. 2 is a graph illustrating gamma correction characteristics of the gamma correction unit in FIG. 1.

Gamma correction unit 32 corrects each pixel value of color image P based on a gamma curve like that shown in FIG. 2. That is, fluorescence L2 is very weak in comparison with excitation light L1, so that a signal value of fluorescence L2 is increased and a signal value of excitation light L1 is attenuated by performing gamma correction on color image P. This allows acquisition of high quality fluorescence image SPr. Noise elimination unit 33 eliminates noise in color image P gamma-corrected by gamma correction unit 32, in which any known method may be used as the noise elimination method. Spectral image generation unit 34 generates an estimated spectral image in which wavelength components of excitation light L1 and fluorescence light L2 are allocated to different primary color components from color image P obtained by image obtaining unit 31 and eliminated of noise by noise elimination unit 33. For details of an example operation of spectral image generation unit 34, refer to Japanese unexamined Patent Publication No. 2003-093336.

More specifically, spectral image generation unit 34 extracts a background image of wavelength component $\Delta\lambda 1$ of the excitation light from color image P by performing a matrix operation shown in Formula (1) below.

$$\begin{bmatrix} R_{SP} \\ G_{SP} \\ B_{SP} \end{bmatrix} = \begin{bmatrix} k_{1r} & k_{1g} & k_{1b} \\ k_{2r} & k_{2g} & k_{2b} \\ k_{1r} & k_{1g} & k_{1b} \end{bmatrix} \times \begin{bmatrix} R_P \\ G_P \\ B_P \end{bmatrix} \quad (1)$$

where, $R_{SP}$, $G_{SP}$, and $B_{SP}$ are RBG components of estimated spectral image P, $R_P$, $G_P$, and $B_P$ are RBG components of color image P, and $k_{1r}$, $k_{1g}$, $k_{1b}$, $k_{2r}$, $k_{2g}$, and $k_{2b}$ are matrix parameters for performing the matrix operation.

Figure 4:
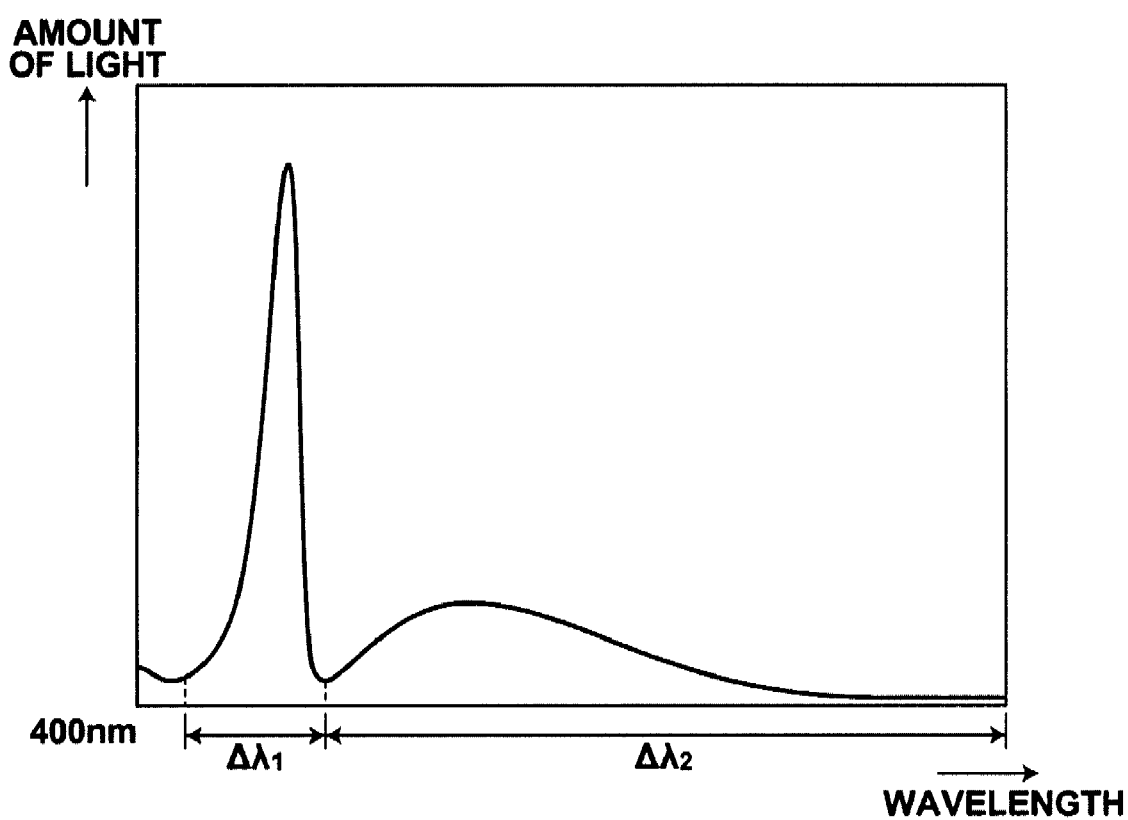
FIG. 4 is a graph illustrating example wavelength ranges of excitation light and self fluorescence.

Here, matrix parameters $Pi=(k_{ri}, k_{gi}, k_{bi})$ (i=1 to 61) with respect to each wavelength range obtained by separating, for example, a wavelength range from 400 to 700 nm by the spacing of 5 nm are stored in parameter database 35, as shown in FIG. 3. FIG. 4 is a graph illustrating example wavelength ranges of excitation light L1 and fluorescence L2 in self fluorescence. As shown in FIG. 4, excitation light L1 has wavelength range $\Delta\lambda 1$ from approximately 405 to 460 nm and fluorescence L2 has wavelength range $\Delta\lambda 2$ from 460 to 700 nm.

Spectral image generation unit 34 obtains parameters $k_{1r}$, $k_{1g}$, and $k_{1b}$ by calculating the sum of each component of matrix parameters Pi within first wavelength range $\Delta\lambda 1$ from matrix parameters Pi stored in parameter database DB. Likewise, spectral image generation unit 34 obtains parameters $k_{2r}$, $k_{2g}$, and $k_{2b}$ by calculating the sum of each component of matrix parameters Pi within second wavelength range $\Delta\lambda 2$. Then, spectral image generation unit 34 generates estimated spectral image SP including background image SPb in which excitation light L1 is allocated to R and G components by Formula (1) above and fluorescence image in which fluorescence L2 is allocated to G component by Formula (1) above.

The intensity of fluorescence light L2 is very weak in comparison with that of excitation light L1, so that a clear fluorescence image can not be obtained by ordinary observation when excitation light L1 is emitted on the subject. But, excitation light L1 and fluorescence light L2 have different wavelength ranges $\Delta\lambda 1$ and $\Delta\lambda 2$ (FIG. 4), and inside of a body cavity, for the most part, is red, so that a component of excitation light L1 reflected by the subject is small. Consequently, fluorescence image SPr of G component of estimated spectral image SP can be obtained by extracting wavelength range $\Delta\lambda 2$ of fluorescence L2. FIGS. 3 and 4 illustrate an example case in which fluorescence L2 is self fluorescence, but it may be, for example, fluorescence L2 of wavelengths adjacent to 636 nm imaged by emitting excitation light L1 of 405 nm wavelength on 5-aminolevulinic acid (ALA) injected inside of a body cavity. Alternatively, it may be, for example, fluorescence L2 of wavelengths adjacent to 840 nm imaged by emitting excitation light L1 of 780 nm wavelength on indocyanine green (ICG) injected inside of the body cavity. Here, each of wavelength ranges $\Delta\lambda 1$ and $\Delta\lambda 2$ of excitation light L1 and fluorescence light L2 are checked in advance, and spectral image generation unit 34 generates estimated spectral image SP in which excitation light L1 and fluorescence light L2 are allocated to different primary color components by performing a matrix operation using matrix parameters corresponding to wavelength ranges $\Delta\lambda 1$ and $\Delta\lambda 2$.

Display control unit 36 shown in FIG. 1 causes display device 3, such as liquid crystal display, CRT display, or the like to display various images. More specifically, display control unit 36 has a function to display color image P obtained by image obtaining unit 31, color image P gamma-corrected by gamma correction unit 32, color image P eliminated of noise by noise elimination unit 33, estimated spectral image SP generated by spectral image generation unit 34, background image SPb and fluorescence image SPr on display device 3 selectively or side by side according to input from input unit 2. Display control unit 36 includes mirror image processing unit 36a that perform mirror image processing, mask generation unit 36b that generates and displays a mask image from the various images, and character generation unit 36c that displays information of the various images as character information, thereby displaying images signal processed in various ways.

Figure 5:
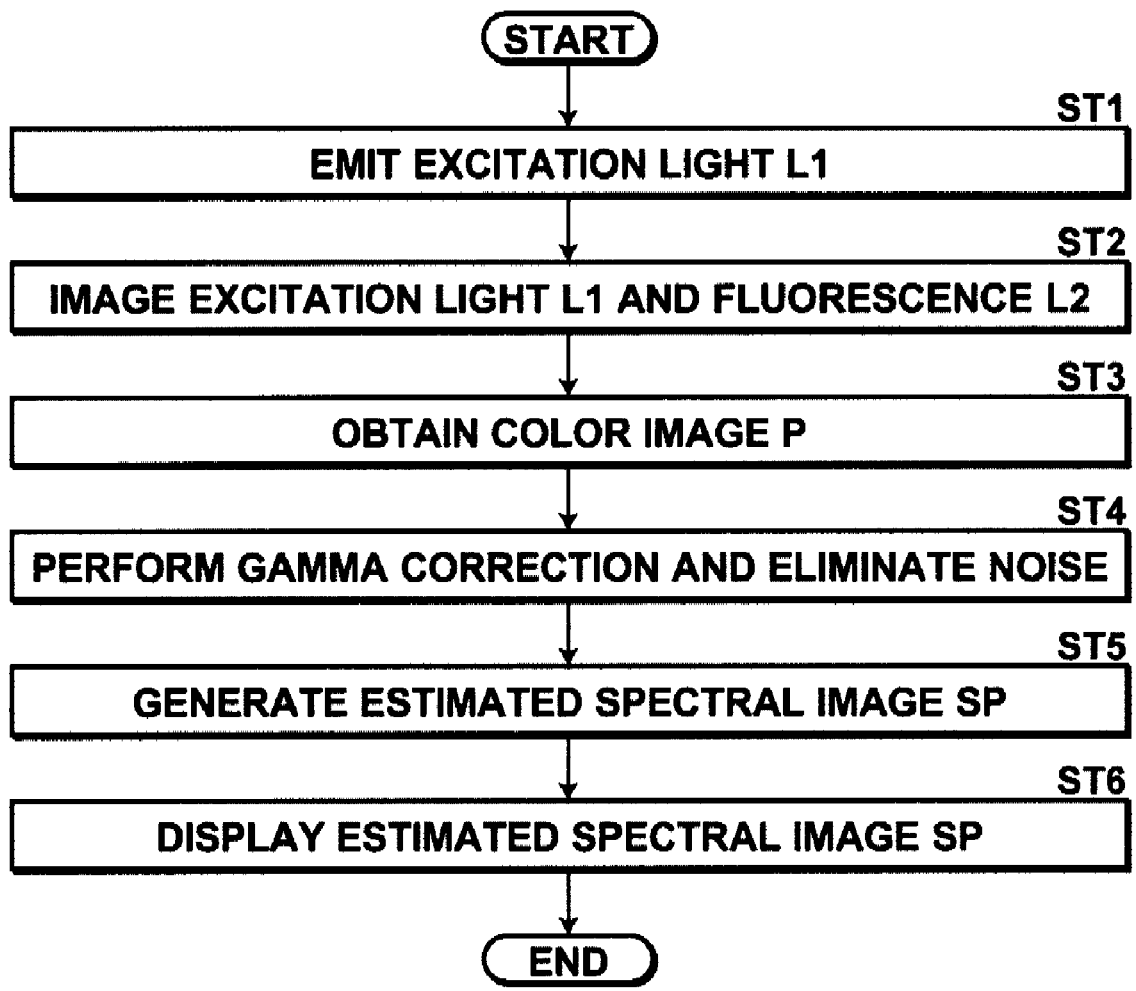
FIG. 5 is a flowchart of the endoscope image processing method according to an exemplary embodiment of the present invention.

FIG. 5 is a flowchart of the endoscope image processing method according to an exemplary embodiment of the present invention. The endoscope image processing method will now be described with reference to FIGS. 1 to 5. First, entire endoscope system 1 is set to fluorescence observation mode for observing self fluorescence via input unit 2. Then, excitation light L1 is outputted from light source unit 10 and emitted on a subject via light guide 15 and observation window 16 (step ST1).

Then, excitation light L1 reflected from the subject and self fluorescence L2 of the subject are obtained by imaging device 22 as color image P (step ST2). The imaged signals are subjected to correlated double sampling and amplified through automatic gain control in CDS/AGC circuit 23, A/D converted in A/D conversion unit 24 and outputted to endoscope image processing apparatus 30.

In endoscope image processing apparatus 30, color image P is obtained by image obtaining unit 31 (step ST3). Thereafter, gamma correction and noise elimination are performed on color image P by gamma correction unit 32 and noise elimination unit 33 respectively (step ST4). Then, in spectral image generation unit 34, a matrix operation is performed using Formula (1) above and matrix data shown in FIG. 3 based on color image P, whereby estimated spectral image SP is generated (step ST5). Generated estimated spectral image SP is displayed on display device 3 by display control unit 36. Here, fluorescence image SPr of G component, estimated spectral image of RGB components, and an image of RB components and representing excitation light are selectively displayed on the display device 3 according to input from input unit 2.

In this way, estimated spectral image SP in which wavelength component $\Delta\lambda 1$ of excitation light L1 and wavelength component $\Delta\lambda 2$ of fluorescence L2 are allocated to different primary color components is obtained. This allows acquisition of fluorescence image SPr with a simple configuration without requiring separate imaging devices as in the past, whereby emission state of fluorescence L2 may be checked. Further, this allows to obtain background image SPb and fluorescence image SPr from the same color image, color image P, so that a difference in position between background image SPb and fluorescence image SPr due to a time difference in obtaining the images may be prevented and a comparison between a region on which excitation light L1 is emitted and a region from which fluorescence L2 is emitted may be made accurately.

Figure 6:
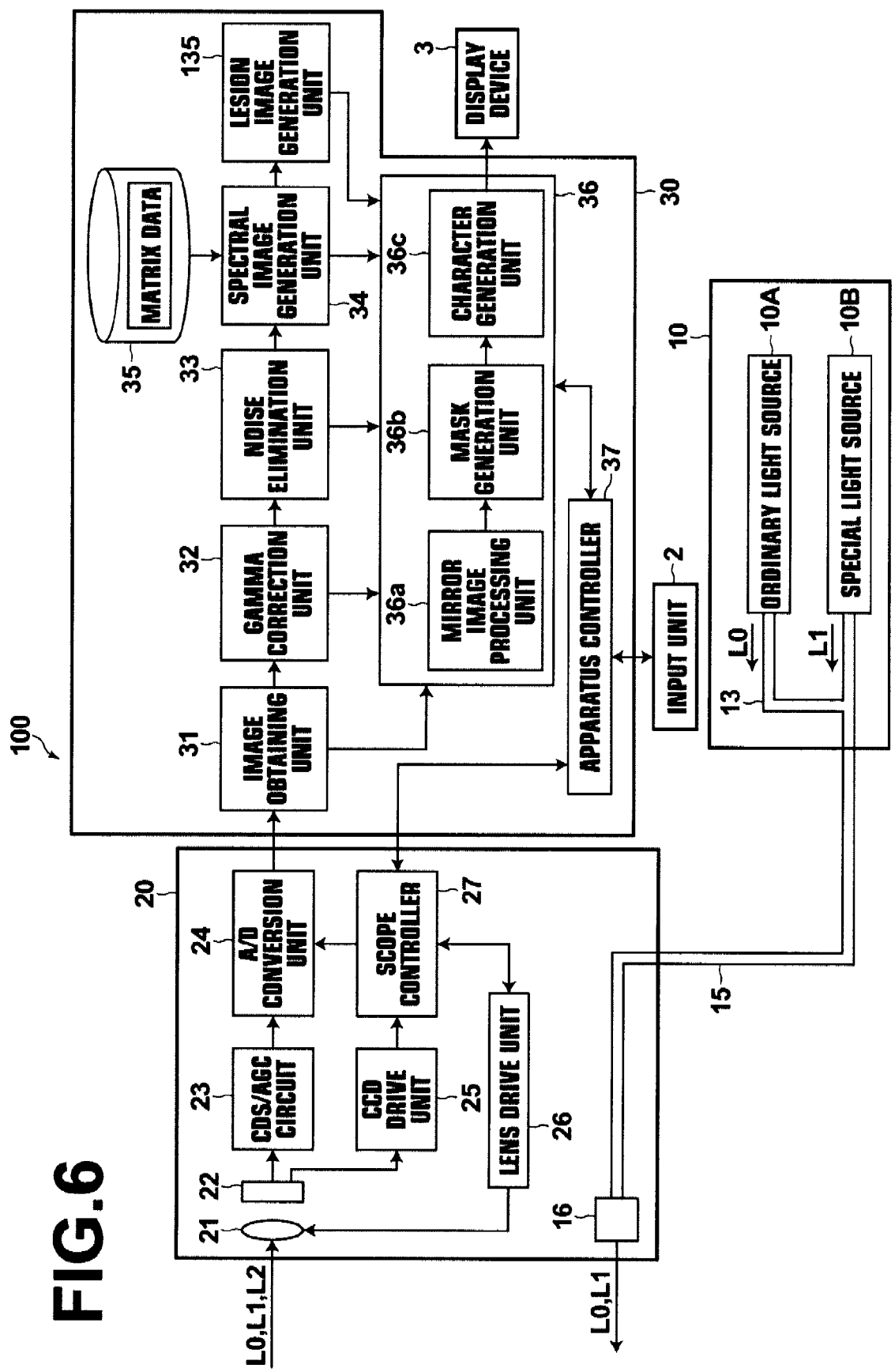
FIG. 6 is a block diagram of the endoscope image processing apparatus according to an alternative embodiment of the present invention.

FIG. 6 is a block diagram of the endoscope image processing apparatus according to an alternative embodiment of the present invention. In endoscope image processing apparatus 130, components identical to those of endoscope image processing apparatus 30 in FIG. 1 are given the same reference numerals and will not be elaborated upon further here. Endoscope image processing apparatus 130 differs from endoscope image processing apparatus 30 in that it further includes lesion image generation unit 135.

Lesion image generation unit 135 calculates a lesion index and generates a lesion index image colored according to the value of the lesion index. More specifically, spectral image generation unit 34 has a function to generate sub-fluorescence image SPr10 of a green wavelength range (about 500 to 550 nm) from color image P or estimated spectral image SP. That is, fluorescence image SPr is an image that indicates the wavelength range from green to red (470 to 700 nm), while sub-fluorescence image SPr10 is an image that indicates the green wavelength range (about 500 to 550 nm) of fluorescence image SPr.

Lesion image generation unit 135 calculates, with respect to each pixel, the ratio of the pixel value in sub-fluorescence image SPr10 to the pixel value in fluorescence image SPr as a lesion index (0.00 to 1.0), and generates a lesion index image colored based on the calculated lesion index values. For example, coloring in which the brightness is increased as the lesion index increases is performed. Then, the generated lesion index image is displayed on display device 3 by display control unit 36 according to input from input unit 2.

In this way, by taking note of the fact that a normal area has a higher proportion of intensity in the green wavelength range in the wavelength range of self fluorescence L2 in comparison with a lesion area, and visualizing the ratio of the green wavelength range from 500 to 550 nm in the fluorescence as a lesion index image, fluorescence diagnosis may be made accurately.

According to each of the embodiments described above, color image P is obtained, when excitation light L1 is emitted on a subject, by imaging excitation light L1 reflected from the subject and fluorescence L2 emitted from the subject, and estimated spectral image SP is generated in which a wavelength component of excitation light L2 and a wavelength component of fluorescence L2 included in obtained color image P are allocated to different primary color components. This allows generation of background image SPb and fluorescence image SPr from color image P based on wavelength information of excitation light L1 and fluorescence L2 without separate imaging devices as required in the past, whereby emission state of fluorescence L2 may be checked with a simple configuration.

Further, where gamma correction unit 32 that performs gamma correction on color image P obtained by image obtaining unit 31 is provided, as shown in FIGS. 1 and 2, and spectral image generation unit 34 is a unit for generating estimated spectral image SP using color image P gamma-corrected by gamma correction unit 32, signal values representing excitation light L1 in estimated spectral image SP may be reduced, and signal values representing fluorescence in estimated spectral image SP may be increased. This allows generation of estimated spectral image SP enhanced in the fluorescence portion.

Further, as shown in FIG. 6, where excitation light L1 is light in a blue wavelength range and fluorescence L2 is self fluorescence, the spectral image generation unit is a unit having a function to generate sub-fluorescence image SPr10 of a green wavelength range from color image P or estimated spectral image SP, and lesion image generation unit 135 for calculating, with respect to each pixel, the ratio of the pixel value of sub-fluorescence image SPr10 to the pixel value of fluorescence image SPr as a lesion index and generating a lesion index image colored based on the calculated lesion index values is further included, accurate fluorescence diagnosis may be made by taking note of the fact that a normal area has a higher proportion of intensity in a green wavelength range in the wavelength range of self fluorescence L2 in comparison with a lesion area, and visualizing the ratio of the green wavelength range from 500 to 550 nm in the fluorescence L2 as a lesion index image.

Further, where scope 20 further includes a cut filter disposed on the light receiving side of imaging device 22 to reduce the amount of excitation light L1 received by the imaging device, then even when the emission amount of excitation light L1 is increased in order to increase the emission amount of fluorescence L2, the imaging device may be prevented from saturating, whereby excitation light L1 and fluorescence L2 may be imaged accurately.

It should be appreciated that embodiments of the present invention are not limited to those described above. For example, Formula (1) above illustrates a case in which wavelength range $\Delta\lambda 1$ of excitation light L1 is allocated to R and B components and wavelength range $\Delta\lambda 2$ of fluorescence L2 is allocated to G component of estimated spectral image SP, but each of excitation light L1 and fluorescence L2 maybe allocated to any of RGB components of estimated spectral image SP.

Further, in the embodiments above, description has been made of a case in which endoscope image processing apparatus 30 is constructed using hardware, such as a DSP and the like, but it may be an endoscope image processing apparatus constituted by a computer, such as a personal computer or the like. In this case, the configuration of endoscope image processing apparatus 30 shown in FIG. 1 is realized by executing endoscope image processing program stored in an auxiliary storage device on the computer (e.g., personal computer).

Still further, in the embodiments above, description has been made of a case in which endoscope system 1 is a system that allows both ordinary observation and fluorescence observation, but the endoscope image processing apparatus 30 may be applied to an endoscope system that allows only fluorescence observation.

What is claimed is:

1. An endoscope image processing method, comprising the steps of:

obtaining a color image, when excitation light is emitted on a subject, by imaging excitation light reflected from the subject and fluorescence emitted from the subject; and generating an estimated spectral image that includes a background image representing the excitation light and a fluorescence image representing the fluorescence by allocating a wavelength component of the excitation light and a wavelength component of the fluorescence included in the obtained color image to different primary color components, wherein:

the wavelength component of the excitation light and the wavelength component of the fluorescence are allocated to different primary color components by administering spectral image processes that employ matrix parameters, to generate the estimated spectral image that includes the background image representing the excitation light and the fluorescence image representing the fluorescence.

2. An endoscope image processing apparatus, comprising:

an image obtaining unit for obtaining a color image, when excitation light is emitted on a subject, by imaging excitation light reflected from the subject and fluorescence emitted from the subject; and a spectral image generation unit for generating an estimated spectral image that includes a background image representing the excitation light and a fluorescence image representing the fluorescence by allocating a wavelength component of the excitation light and a wavelength component of the fluorescence included in the obtained color image to different primary color components, wherein:

the spectral image generation unit allocates the wavelength component of the excitation light and the wavelength component of the fluorescence to different primary color components by administering spectral image processes that employ matrix parameters, to generate the estimated spectral image that includes the background image representing the excitation light and the fluorescence image representing the fluorescence.

3. The endoscope image processing apparatus as claimed in claim 2, wherein:

the apparatus further comprises a gamma correction unit for performing gamma correction on the color image obtained by the image obtaining unit; and the spectral image generation unit is a unit for generating the estimated spectral image using the color image gamma-corrected by the gamma correction unit.

4. The endoscope image processing apparatus as claimed in claim 2, wherein:

the excitation light has a blue wavelength range and the fluorescence is self fluorescence;

the spectral image generation unit is a unit for generating the estimated spectral image using matrix parameters corresponding to the wavelength range of the excitation light, and matrix parameters corresponding to the wavelength range of the fluorescence.

5. The endoscope image processing apparatus as claimed in claim 4, wherein:

the spectral image generation unit is a unit having a function to generate a sub-fluorescence image of a green wavelength range from the color image or the estimated spectral image; and the apparatus further includes a lesion image generation unit for calculating, with respect to each pixel, the ratio of the pixel value of the sub-fluorescence image to the pixel value of the fluorescence image as a lesion index, and generating a lesion index image colored based on the calculated lesion index values.

6. The endoscope image processing apparatus as claimed in claim 2, wherein the excitation light has a blue wavelength range, and the fluorescence is fluorescence emitted from the subject stained by 5-aminolevulinic acid.

7. The endoscope image processing apparatus as claimed in claim 2, wherein the excitation light is infrared light, and the fluorescence is fluorescence emitted from the subject stained by indocyanine green.

8. An endoscope system comprising:

a light source unit for emitting excitation light on a subject;

a scope for guiding the excitation light emitted from the light source unit to the subject and having an imaging device for imaging, when the excitation light is emitted on the subject, excitation light reflected from the subject and fluorescence emitted from the subject; and an endoscope image processing apparatus for extracting a fluorescence image from a subject image obtained by the scope, wherein the endoscope image processing apparatus includes:

an image obtaining unit for obtaining a color image taken by the imaging device; and a spectral image generation unit for generating an estimated spectral image that includes a background image representing the excitation light and a fluorescence image representing the fluorescence by allocating a wavelength component of the excitation light and a wavelength component of the fluorescence included in the obtained color image to different primary color components, wherein:

the spectral image generation unit allocates the wavelength component of the excitation light and the wavelength component of the fluorescence to different primary color components by administering spectral image processes that employ matrix parameters, to generate the estimated spectral image that includes the background image representing the excitation light and the fluorescence image representing the fluorescence.

9. The endoscope system as claimed in claim 8, wherein the scope further comprises a cut filter disposed on the light receiving surface side of the imaging device to reduce the amount of light in the wavelength range of the excitation light received by the imaging device.

* * * * *